US009822376B2

(12) United States Patent
Vance et al.

(10) Patent No.: US 9,822,376 B2
(45) Date of Patent: Nov. 21, 2017

(54) COMPOSITIONS AND METHODS FOR THE MODULATION OF GENE EXPRESSION IN PLANTS

(75) Inventors: Viki Bowman Vance, Columbia, SC (US); Lewis Howard Bowman, Columbia, SC (US); Allison Mallory, Paris (FR)

(73) Assignee: University of South Carolina, Columbia, SC (US)

( * ) Notice: Subject to any disclaimer, the term of this patent is extended or adjusted under 35 U.S.C. 154(b) by 1231 days.

(21) Appl. No.: 13/282,680

(22) Filed: Oct. 27, 2011

(65) Prior Publication Data

US 2012/0100613 A1 Apr. 26, 2012

Related U.S. Application Data

(62) Division of application No. 10/623,930, filed on Jul. 21, 2003, now abandoned.

(60) Provisional application No. 60/397,487, filed on Jul. 19, 2002.

(51) Int. Cl.
*A01H 5/00* (2006.01)
*C12N 15/82* (2006.01)

(52) U.S. Cl.
CPC ....... *C12N 15/821* (2013.01); *C12N 15/8216* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 4,684,611 A | 8/1987 | Schilperoort et al. | |
| 4,945,050 A | 7/1990 | Sanford et al. | |
| 5,023,179 A | 6/1991 | Lam et al. | |
| 5,100,792 A | 3/1992 | Sanford et al. | |
| 5,110,732 A | 5/1992 | Benfey et al. | |
| 5,240,855 A | 8/1993 | Tomes | |
| 5,268,463 A | 12/1993 | Jefferson | |
| 5,322,783 A | 6/1994 | Tomes et al. | |
| 5,324,646 A | 6/1994 | Buising et al. | |
| 5,380,831 A | 1/1995 | Adang et al. | |
| 5,399,680 A | 3/1995 | Zhu et al. | |
| 5,401,836 A | 3/1995 | Baszczynski et al. | |
| 5,428,148 A | 6/1995 | Reddy et al. | |
| 5,436,391 A | 7/1995 | Fujimoto et al. | |
| 5,459,252 A | 10/1995 | Conkling et al. | |
| 5,466,785 A | 11/1995 | de Frammond | |
| 5,563,055 A | 10/1996 | Townsend et al. | |
| 5,569,597 A | 10/1996 | Grimsley et al. | |
| 5,604,121 A | 2/1997 | Hilder et al. | |
| 5,608,142 A | 3/1997 | Barton et al. | |
| 5,608,144 A | 3/1997 | Baden et al. | |
| 5,608,149 A | 3/1997 | Barry et al. | |
| 5,633,363 A | 5/1997 | Colbert et al. | |
| 5,659,026 A | 8/1997 | Baszczynski et al. | |
| 5,750,386 A | 5/1998 | Conkling et al. | |
| 5,789,156 A | 8/1998 | Bujard et al. | |
| 5,814,618 A | 9/1998 | Bujard et al. | |
| 5,837,876 A | 11/1998 | Conkling et al. | |
| 5,939,541 A | 8/1999 | Vance et al. | |
| 6,395,962 B1 | 5/2002 | Vance | |
| 2004/0053411 A1* | 3/2004 | Cullen et al. | 435/455 |
| 2005/0120415 A1 | 6/2005 | Aukerman | |
| 2005/0138689 A1 | 6/2005 | Aukerman | |
| 2006/0218673 A9 | 9/2006 | Aukerman | |

FOREIGN PATENT DOCUMENTS

| | | |
|---|---|---|
| DE | 4005152 | 8/1991 |
| EP | 0116718 | 8/1984 |
| EP | 0175966 | 4/1986 |
| EP | 0270355 | 6/1988 |
| EP | 0290395 | 11/1988 |
| EP | 0331083 | 9/1989 |
| EP | 0434616 | 6/1991 |
| EP | 0444882 | 9/1991 |
| EP | 0486233 | 5/1992 |
| EP | 0486234 | 5/1992 |
| EP | 1551967 | 8/2011 |
| WO | WO 87/06614 | 11/1987 |
| WO | WO 90/12096 | 10/1990 |
| WO | WO 92/09696 | 6/1992 |

(Continued)

OTHER PUBLICATIONS

Llave et al. (The Plant Cell, 14:1605-1619, 2002).*
Reinhart et al. (Genes and Development, 16:1616-1626, 2002).*
Baga et al. (Expression and Regulation for selection of transformants and modification of traits in cereals (1999). In Vasil et al. (eds), Advances in Cellular and Molecular Biology of Plants, 5: 85-131, Springer-Science+Business Media Dordrecht, Germany).*
Allen, et al. "microRNA-Directed Phasing during Trans-Acting siRNA Biogenesis in Plants", *Cell*, vol. 121, 207-221, Apr. 22, 2005.
Allison et al. "The nucleotide sequence of the coding region of tobacco etch virus genomic RNA: Evidence for the synthesis of a single polyprotein," *Virology* 154:9-20 (1986).

(Continued)

*Primary Examiner* — Vinod Kumar
(74) *Attorney, Agent, or Firm* — Dority & Manning, PA

(57) ABSTRACT

Compositions and methods for modulating nucleotide sequence expression, particularly for modulating gene expression in plants, are provided. The compositions comprise precursor RNA constructs for the expression of an RNA precursor. The precursor RNA construct comprises a promoter that is expressed in a plant cell driving the expression of a precursor RNA having a microRNA. The miRNA is complementary or partially complementary to a portion of a target gene or nucleotide sequence and function to modulate expression of the target sequence or gene. In this manner, the RNA precursor construct can be designed to modulate expression of any nucleotide sequence of interest, either an endogenous plant gene or alternatively a transgene. Transformed plants, tissues, cells and seeds are also provided.

8 Claims, 2 Drawing Sheets

(56) References Cited

FOREIGN PATENT DOCUMENTS

| | | |
|---|---|---|
| WO | WO 94/00583 | 1/1994 |
| WO | WO 98/36083 | 8/1998 |
| WO | WO 98/44097 | 10/1998 |
| WO | WO 99/15682 | 4/1999 |
| WO | WO 01/38512 | 5/2001 |
| WO | WO 03/093441 | 11/2003 |
| WO | WO 2005/035769 | 4/2005 |

OTHER PUBLICATIONS

Altschul et al. "Gapped BLAST and PSI-BLAST: a new generation of protein database search programs," *Nucleic Acid Research* 25(17):3389-3402 (1997).

Altschul, et al. "Basic Local Alignment Search Tool," *Journal of Molecular Biology* 215:403-410 (1990).

Alvarez et al. "Endogenous and synthetic microRNAs stimulate simultaneous, efficient, and localized regulation of multiple targts in diverse species," *The Plant Cell* 18(5):1134-1151 (2006) Epub Apr 7, 2006.

An, G. "High Efficiency Transformation of Cultured Tobacco Cells," *Plant Physiology* 79:568-570 (1985).

Anandalakshmi et al. "A Calmodulin-Related Protein That Suppresses Posttranscriptional Gene Silencing in Plants," *Science* 290:142-144 (2000).

Anandalakshmi et al. "A viral suppressor of gene silencing in plants," *Proceedings of the National Academy of Sciences of the United States of America* 95:13079-13084.

Angell at al. "Consistent gene silencing in transgenic plants expressing a replicating potato virus X RNA," *EMBO Journal* 16(12):3675-3684 (1997) Oxford University Press.

Ballas et al. "Efficient functioning of plant promoters and poly(A) sites in *Xenopus* oocytes," *Nucleic Acids Research* 17(19):7891-7903 (1989).

Bartel et al. "MicroRNAS: At the Root of Plant Development?" *Plant Physiology* 132:709-717 (2003).

Bevan "Binary *Agrobacterium* vectors for plant transformation," *Nucleic Acid Research* 12(22):8711-8721 (1984).

Bogusz et al. "Nonlegume Hemoglobin Genes Retain Organ-Specific Expression in Heterologous Transgenic Plants," *The Plant Cell* 2(7):633-641 (1990).

Brigneti et al. "Viral pathogenicity determinants are suppressors of transgene silencing in *Nicotiana benthamiana*," *EMBO Journal* 17(22):6739-6746 (1998).

Bytebier et al. "T-DNA Organization in Tumor Cultures and Transgenic Plants of the Monocotyledon Asparagus officinalis," *Proceedings of the National Academy of Sciences of the United States of America* 84(15):5345-5349 (1987).

Canevascini et al. "Tissue-Specific Expression and Promoter Analysis of Tobacco Itp1 Gene," *Plant Physiology* 112:513-524 (1996).

Cao et al. "Regeneration of herbicide resistant transgenic rice plants following nnicroprojectile-mediated transformation of suspension culture cells," *Plant Cell Reports* 11(11):586-591 (1992).

Capone et al. "Expression in different populations of cells of the root meristem is controlled by different domains of the rolB promoter," *Plant Molecular Biology* 25(4):681-691 (1994).

Carrington et al. "Expression of potyviral polyproteins in transgenic plants reveals three proteolytic activities required for complete processing," *EMBO Journal* 9(5):1347-1353 (1990).

Chapman et al. "Viral RNA Silencing Suppressors Inhibit the microRNA Pathway at an Intermediate Step," *Genes and Development* 18:1179-1186 (2004).

Chen, et al., "MicroRNAs Modulate Hematopoietic Lineage Differentiation", *Science*, vol. 303, Jan. 2, 2004.

Christensen et al. "Maize polyubiquitin genes: structure, thermal perturbation of expression and transcript splicing, and promoter activity following transfer to protoplasts by electroporation," *Plant Molecular Biology* 18:675-689 (1992).

Christensen, A. & Quail, P. "Sequence analysis and transcriptional regulation by heat shock of polyubiquiting transcripts from maize," *Plant Molecular Biology* 12(6):619-632 (1989).

Christou et al. "Stable transformation of soybean callus by DNA-coated gold particles," *Plant Physiology* 87(3):671-674 (1988).

Christou, P. & Ford, T. "Recovery of Chimeric Rice Plants from Dry Seed using Electric Discharge Particle Acceleration," *Annals of Botany* 75:449-454 (1995).

Cordero et al. "Expression of a maize proteinase inhibitor gene is induced in response to wounding and fungal infection: systemic wound-response of a monocot gene," *The Plant Journal* 6(2):141-150 (1994).

Cordero et al. "Induction of PR proteins in germinating maize seeds infected with the fungus *Fusarium moniliforme*," *Physiological and Molecular Plant Pathology* 41(3):189-200 (1992).

Corpet, F. "Multiple sequence alignment with hierarchical clustering," *Nucleic Acids Res.* 16(22):10881-10890 (1988).

Crossway et al. "Micromanipulation Techniques in Plant Biotechnology," *Biotechniques* 4:320-334 (1986).

D'Halluin et al. "Transgenic Maize Plants by Tissue Electroporation," *The Plant Cell* 4(12):1495-1505 (1992).

Della-Cioppa et al. "Protein Trafficking in Plant Cells," *Plant Physiology* 84:965-968 (1987).

Duan et al. "Transgenic rice plants harboring an introduced potato proteinase inhibitor II gene are insect resistant," *Nature Biotechnology* 14:494-498 (1996).

Eckelkamp et al. "Wound-induced systemic accumulation of a transcript coding for a Bowman-Birk trypsin inhibitor-related protein in maize (*Zea mays* L.) seedlings," *FEBS Letters* 323(1-2):73-76 (1993).

Elmayan et al. "Expression of Single Copies of a Strongly Expressed 35S Transgene Can be Silenced Post-transcriptionally," *The Plant Journal* 9(6):787-797 (1996).

Elroy-Stein et al. "Cap-independent translation of mRNA conferred by encephalomyocarditis virus 5' sequence improves the performance of the vaccinia virus/bacteriophage T7 hybrid expression system," *Proceedings of the National Academy of Sciences of the United States of America* 86:6126-6130 (1989).

Finer, J. & McMullen, M. "Transformation of soybean via particle bombardment of embryogenic suspension culture tissue," *In Vitro Cellular & Developmental Biology* 27(4):175-182 (1991).

Finnegan et al. "Posttranscriptional Gene Silencing is not Compromised in the Arabidopsis Carpel Factory (DICER-LIKE1) Mutant, a Homolog of Dicer-1 from *Drosophila*," *Current Biology* 13:236-240 (2003).

Freeman et al. "A Comparison of Methods for Plasmid Delivery into Ipant Protoplasts," *Plant Cell Physiology* 25(8):1353-1365 (1984).

Gatz et al. "Regulation of a modified CaMV 358 promoter by the Tn10-encoded Tet repressor in transgenic tobacco," *Molecular and General Genetics* 227(2):229-237 (1991).

Gotor et al. "Analysis of three tissue-specific elements from the wheat Cab-I enhancer," *Plant Journal* 3(4):509-518 (1993).

Griffiths-Jones et al. "miRBase: microRNA sequences, targets and gene nomenclature," *Nucleic Acids Res.* 34(Database issue):D140-144 (2006).

Guerineau et al. "Effect of deletions in the cauliflower mosaic virus polyadenylation sequence on the choice of the polyadenylation sites in tobacco protoplasts," *Molecular and General Genetics* 226(1-2):141-144 (1991).

Guevara-Garcia et al. "Tissue-specific and wound-inducible pattern of expression of the mannopine synthase promoter is determined by the interaction between positive and negative cis-regulatory elements," *The Plant Cell* 4(3):495-505 (1993).

Hamilton et al. "Two classes of short interfering RNA in RNA silencing," *EMBO Journal* 21:4671-4679 (2002) 4.

Hannon, G., "RNA Interference", *Nature*, vol. 418, Jul. 11, 2002.

Hansen et al. "Ti Wound-inducible and organ-specific expression of ORF13 from Agrobacterium rhizogenes 8196 T-DNA in transgenic tobacco plants," *Molecular and General Genetics* 254(3):337-343 (1997).

Henikoff, S. and Henikoff, J. "Amino acid substitution matrices from protein blocks," *Proceedings of the National Academy of Sciences of the United States of America* 89:10915-10919 (1992).

(56) References Cited

OTHER PUBLICATIONS

Hiei et al. "Efficient transformation of rice (*Oryze sativa* L.) mediated by *Agrobacterium* and sequence analysis of the boundaries of the T-DNA," *The Plant Journal* 6(2):271-282 (1994).
Higgins, D. & Sharp, P. "CLUSTAL: a package for performing multiple sequence alignment on a microcomputer," *Gene* 73(1):237-244 (1988).
Higgins, D. & Sharp, P. "Fast and sensitive multiple sequence alignments on a microcomputer," *CABIOS* 5:151-153 (1989).
Hobbs et al. "The effect of T-DNA copy number, position and mehtylation on reporter gene expression in tobacco transformants," *Plant Molecular Biology* 15(6):851-864 (1990).
Hooykass-Van Slogteren et al. "Expression of Ti plasmid genes in monocotyledonus plants infected with *Agrobacterium tumefaciens*," *Nature* (London) 311:763-764 (1984).
Huang et al. "Parallelization of a local similarity algorithm," *CABIOS* 8(2):155-165 (1992).
Hunter et al. "Missing Links: miRNAs and plant development," *Current Opinion in Genetics and Development* 13:372-378 (2003).
Ishida et al. "High efficiency transformation of maize (*Zea mays* L.) mediated by *Agrobacterium tumefaciens*," *Nature Biotechnology* 14:745-750 (1996).
Jobling, S. & Gehrke, L. "Enhanced translation of chimaeric messenger RNAs containing a plant viral untranslated leader sequence," *Nature* 325:622-624 (1987).
Johansen et al. "Silencing on the spot. Induction and suppression of RNA silencing in the Agrobacterium-mediated transient expression system," *Plant Physiology* 126(3):930-938 (2001).
Joshi "Putative polyadenylation signals in nuclear genes of higher plants: a compilation and analysis," *Nucleic Acids Research* 15(23):9627-9640 (1987).
Kaeppler et al. "Silicon carbide fiber-mediated DNA delivery into plant cells," *Plant Cell Reports* 9:415-418 (1990).
Kaeppler et al. "Silicon carbide fiber-mediated stable transformation of plant cells," *Theoretical and Applied Genetics* 84:560-566 (1992).
Karlin, S. & Altschul, S. "Applications and statistics for multiple high-scoring segments in molecular sequences," *Proceedings of the National Academy of Sciences of the United States of America* 90(120):5873-5877 (1993).
Karlin, S. & Altschul, S. "Methods for Assessing the Statistical Significance of Molecular Sequence Features by Using General Scoring Schemes," *Proceedings of the National Academy of Sciences of the United States of America* 87(6):2264-2268 (1990).
Kasschau et al. "P1/HC-Pro, a Viral Suppressor of Rna Silencing, interferes with *Arabidopsis* Development and miRNA Function." *Developmental Cell* 4(2):205-217 (2003).
Kawamata et al. "Temporal and Spatial Pattern of Expression of the Pea Phenylalanine Ammonia-Lyase Gene1 Promoter in Transgenic Tobacco," *Plant & Cell Physiology* 38(7):792-803 (1997).
Keller, B. & Baumgartner, C. "Vascular-Specific Expression of the Bean GRP 1.8 Gene is Negatively Regulated," *The Plant Cell* 3(10):1051-1061 (1991).
Kidner et al. "Macro Effects of microRNAs in plants" *Trends in Genetics* 16:13-16 (2003).
Kindle "High-frequency nuclear transformation of *Chlamydomonas reinhardtii*," *Proceedings of the National Academy of Sciences of the United States of America* 87:1228-1232 (1990).
Klein et al. "Genetic Transformation of Maize Cells by Particle Bombardment," *Plant Physiology* 91:440-440 (1989).
Klein et al. "Transfer of foreign genes into intact maize cells with high-velocity microprojectiles," *Proceedings of the National Academy of Sciences of the United States of America* 85(12):4305-4309 (1988).
Kunkel et al. "Rapid and efficient site-specific mutagenesis without phenotypic selection," *Methods in Enzymology* 154:367-382 (1987).
Kunkel, TA. "Rapid and efficient site-specific mutagenesis without phenotypic selection," *Proceedings of the National Academy of Sciences of the United States of America* 82(2):488-492 (1985).

Kuster et al. "The promoter of the *Vicia faba* L. VfENOD-GRP3 gene encoding a glycine-rich early nodulin mediates a predominant gene expression in the interzone II-III region of transgenic Vicia hirsute root nodules," *Plant Molecular Biology* 29(4):759-772 (1995).
Kwon et al. "Identification of a Light-Responsive Region of the Nuclear Gene Encoding the B Subunit of Chloroplast Glyceraldehyde 3-Phosphate Dehydrogenase from *Arabidopsis thaliana*," *Plant Physiology* 105:357-367 (1994).
Lagos-Quintana et al. "Identification of novel Genes Coding for Small Expressed RNAs," *Science* 294:853-857 (2001) American Association for the Advancement of Science, USA.
Last et al. "pEmu: an improved promoter for gene expression in cereal cells," *Theoretical and Applied Genetics* 81(5):581-588 (1991).
Lau et al. "An Abundant Class of Tiny RNAs with Probable Regulatory Roles in *Caenorhabditis elegans*," *Science* 294:858-861 (2001) American Association for the Advancement of Science, USA.
Leach, F. & Aoyagi, K "Promoter analysis of the highly expressed rolC and rolD root-inducing genes of *Agrobacterium rhizogenes:* enhancer and tissue-specific DNA determinants are dissociated," *Plant Science* 79(1):69-76 (1991).
Lee et al. "An Extensive Class of Small RNAs in *Caenorhabditis elegans*," *Science* 294:862-864 (2001) American Association for the Advancement of Science, USA.
Lee et al. "MicroRNA maturation: stepwise processing and subcellular localization," *EMBO Journal* 21(17):4663-4670 (2002) European Molecular Biology Organization.
Li et al. "An improved rice transformation system using the biolistic method," *Plant Cell Reports* 12(5):250-255 (1993).
Llave et al. "Virus-encoded suppressor of posttranscriptional gene silencing targets maintenance step in the silencing pathway," *PNAS* 97(24):13401-13406 (2000).
Llave et al., "Cleaage of Scarecrow-line mRNA targets directed by a class of Arabidopsis miRNA," *Science* 297(5589):2053-2056 (2002).
Llave et al., "Endogenous and Silencing-Associated Small RNAs in Plants", *The Plant Cell*, 14:1605-1619 (2002).
Lommel et al. "Identification of the Maize chlorotic mottle virus capsid protein cistron and characterization of its subgenomic messenger RNA," *Virology* 181(2):382-385 (1991).
Lu, et al, "RNA Silencing in Plants by the Expression of siRNA duplexes", *Nucleic Acids Research*, 2004, vol. 32, No. 21.
Macejak, D. & Sarnow, P. "Internal initiation of translation mediated by the 5' leader of a cellular mRNA," *Nature* 353:90-93 (1991).
Mallory et al. "MicroRNAs: something important between the genes," *Current Opinion in Plant Biology* 14(7):120-125 (2004).
Mallory et al., "MicroRNA control of PHABULOSA in leaf development: importance of pairing to the microRNA 5' region", *The EMBO Journal*, (2004), 23, pp. 3356-3364.
Mallory et al. "The Amplicon-Plus System for High-level Expression of Transgenes in plants," *Nature Biotechnology* 20:622-625 (2002).
Mallory et al., "A viral suppressor of RNA silencing differentially regulates the accumulation of short interfering RNAs and micro-RNAs in tobacco", *PNAS*, 99(23):15228-15233 (2002).
Mallory et al., "HC-Pro suppression of transgene silencing eliminates the small RNAs but not transgene methylation or the mobile signal", *The Plant Cell*, 13:571-583 (2001).
Marineau et al. "Differential accumulation of potato tuber mRNAs during the ypersensitive response induced by arachidonic acid elicitor," *Plant Molecular Biology* 4:335-342 (1987).
Matsuoka et al. "Tissue-specific light-regulated expression directed by the promoter of a C4 gene, maize pyruvate, orthophosphate dikinase, in a C3 plant, rice," *PNAS* 90(20):9586-9590 (1993).
Matton, D. & Brisson, N. "Clong, Expression, and Sequence Conservation of Pathogenesis-Related Gene Transcripts of Potato," *Molecular Plant-Microbe Interactions* 2(6):325-331 (1989).
McCabe et al. "Stable transformation of Soybean (*Glycine max*) by particle acceleration," *Bio/Technology* 6:923-926 (1988).
McElroy et al. "Isolation of an Efficient Actin promoter for Use in Rice Transformation," *The Plant Cell* 2(2):163-171 (1990).

(56) References Cited

OTHER PUBLICATIONS

McGurl et al. "Structure, expression, and antisense inhibition of the systemin precursor gene," *Science* 225:1570-1573 (1992).
McManus et al. "Gene Silencing Using Micro-RNA Designed Hairpins," *RNA* 8:842-850 (2002) Cambridge University Press, UK.
McNellis et al. "Glucocorticoid-inducible expression of a bacterial avirulence gene in transgenic *Arabidopsis* induces hypersensitive cell death," *The Plant Journal* 14(2):247-257 (1998).
Meinkoth, J. & Wahl, G. "Hybridization of nucleic acids immobilized on solid supports," *Analytical Biochemistry* 138:267-284 (1984).
Miao et al. "Ammonia-Regulated Expression of a Soybean Gene Encoding Cytosolic Glutamine Synthetase in Transgenic Lotus corniculatus," *The Plant Cell* 3(1):11-22 (1991).
Mlotshwa et al. "Ectopic DICER-LIKE1 Expression in P1/HC-Pro *Arabidopsis* rescues Phenotypic Anomalies but Not Defects in MicroRNA and Silencing Pathways," *The Plant Cell* 17:2873-2885 (2005).
Mogen et al. "Upstream sequences other than AAUAAA are required for efficient messenger RNA 3[prime]-end formation in plants," *The Plant Cell* 2(12):1261-1272 (1990).
Munroe, D. & Jacobson, A. "Tales of poly(A): a review," *Gene* 91:151-158 (1990).
Murray et al. "Codon usage in plant genes," *Nucleic Acid Research* 17(2)477-498 (1989).
Myers, E. & Miller, W. "Optimal alignments in linear space," *CABIOS* 4(1):11-17 (1988).
Needleman, S. & Wunsch, C. "A general method applicable to the search for similarities in amino acid sequence of two proteins," *Journal of Molecular Biology* 48(3):443-453 (1970).
Niu et al. "Expression of artifical microRNAs in transgenic Arabidopsis thaliana confers virus resistance," *National Biotechnology* 24(11):1420-1428 (2006).
Oard "Physical method for the transformation of plant cells," *Biotechnology Advances* 9:1-11 (1991).
Odell et al. "Identification of DNA sequences required for activity of the cauliflower mosaic virus 35S promoter," *Nature* 313:810-812 (1985).
Papp et al. "Evidence for Nuclear Processing of Plant Micro RNA and Short interfering RNA Precursors," *Plant Physiology* 132:1382-1390 (2003) American Society of Plant Biologists.
Paszkowski et al. "Direct gene transfer to plants," *EMBO Journal* 4(12):2717-2711 (1984).
Pearson et al. "Using the FASTA Program to Search protein and DNA Sequence Databases," *Methods in Molecular Biology* 24:307-331 (1994).
Pearson, W. & Lipman, D. "Improved Tools for Biological Sequence Comparison," *Proceedings of the National Academy of Sciences of the United States of America* 85(8):2444-2448 (1988).
Proudfoot "Poly(A) signals," *Cell* 64:671-674 (1991).
Rathore et al. "Use of bas as a selectable marker gene and for the production of herbicide-resistant rice plants from protoplasts," *Plant Molecular Biology* 21(5):871-884 (1993).
Redolfi, P. "Occurrence of pathogenesis-related (b) and similar proteins in different plant species," *European Journal of Plant Pathology* 89(6):245-254 (1983).
Reinhart, et al., "MicroRNAs in plants", *Genes and Development* 16:1616-1626 (2002).
Rhoades et al. "Prediction of Plant MicroRNA Targets," *Cell* 110(4):513-520 (2002).
Riggs, C. & Bates, G. "Stable transformation of tobacco by electroporation: evidence for plasmid concatenation," *Proceedings of the national Academy of Sciences of the United States* 83(15):5602-5606 (1986).
Rinehart et al. "Tissue-specific and Developmental Regulation of Cotton Gene FbL2A (Demonstration of Promoter Activity in Transgenic Plants)," *Plant Physiology* 112(3):1331-1341 (1996).
Reinhart, eta l., "MicroRNAs in Plants", *Genes and Development*, 16:1616-1626, May 22, 2002.

Rohrmeier, T. & Lehle, L. "WIP1, a wound-inducible gene from maize with homology to Bowman-Birk proteinase inhibitors," *Plant Molecular Biology* 22(5):783-792 (1993).
Russel, D. & Fromm, M. "Tissue-specific expression in transgenic maize of four endosperm promoters from maize and rice," *Transgenic Research* 6(2):157-168 (1997).
Ryan, C.A. "Protease Inhibitors in plants: Genes for Improving Defenses Against Insects and Pathogens," *Annual Review of Phytopathology* 28:425-449 (1990).
Sanfacon et al. "A dissetion of the cauliflower mosaic virus polyadenylation signal," *Genes & Development* 5(1):141-149 (1991).
Sanford et al. "Delivery of substances into cells and tissues using a particle bombardment process," *Particulate Science and Technology* 5:27-37 (1987).
Sanger et al. "Characteristics of a strong promoter from figwort mosaic virus: comparison with the analogous 35S promoter from cauliflower mosaic virus and the regulated mannopine synthase promoter," *Plant Molecular Biology* 14(3):433-443 (1990).
Schena et al. "A steroid-inducible gene expression system for plant cells," *Proceedings of the National Academy of Sciences of the United States of America* 88:10421-10425 (1991).
Schwab et al. "Highly Specific Gene Silencing by Artificial microRNAs in *Arabidopsis*," *The Plant Cell* 18:1121-1133.
Schwab, et al., "Specific Effects of MicroRNAs on the Plant Transcriptome", *Developmental Cell*, vol. 8, pp. 517-527, Apr. 2005.
Shimamoto et al. "Fertil transgenic rice plants regenerated from transformed protoplasts," *Nature* 338:274-276 (1989).
Shimamoto, K. "Gene expression in transgenic monocots," *Current Opinions in Biotechnology* 5(2):158-162 (1994).
Shouse, B. "MicroRNA Turns a New Leaf", *ScienceNow*, 2002 (708): 3.
Siebertz et al. "cis-analysis of the wound-inducible promoter wun1 in transgenic tobacco plants and histochemical localization of its expression," *The Plant Cell* 1(10):961-968 (1989).
Singh et al. "Cytological characterization of transgenic soybean," *Theoretical and Applied Genetics* 96(2):319-324 (1998).
Smith et al. "Comparison of biosequences," *Advances in Applied Mathematics* 2(4):482-489 (1981).
Somssich et al. "Gene structure and in situ transcript localization of pathogenesis-related protein 1 in parsley," *Molecular and General Genetics* 213(1):93-98 (1988).
Somssich et al. "Rapid activation by fungal elicitor of genes encoding 'pathogenesis-related' proteins in cultured parsley cells," *Proceedings of the National Academy of Sciences of the United States of America* 83:2427-2430 (1986).
Stanford et al. "Differential expression within a family of novel wound-induced genes in potato," *Molecular and General Genetics* 215(2):200-208 (1989).
Teeri et al. "Gene fusions to lacZ reveal new expression patterns of chimeric genes in transgenic plants," *EMBO Journal* 8(2):343-350 (1989).
Thompson, G. & Larkins, B. "Structural elements regulating zein gene expression," *BioEssays* 10:108-113 (1989).
Tomes et al. Direct DNA Transfer into Intact Plant Cells via Microprojectile Bombardment. Plant Cell, Tissue, and Organ Culture: Fundamental Methods. 1995.
Uknes et al. "Acquired Resistance in Arabidopsis," *The Plant Cell* 4(6):645-656 (1992).
Vain et al. "Foreign gene delivery into monocotyledonous species," *Biotechnology Advances* 13(4):653-671 (1995).
Valvekens et al., "Agrobacterium tumefaciens-mediated transformation of Arabidopsis thaliana root explants by using kanamycin selection", *PNAS* 85(15):5536-5540 (1988).
Van Camp et al. "Tissue-specific Activity of Two Manganese Superoxide Dismutase Promoters in Transgenic Tobacco," *Plant Physiology* 112:525-535 (1996).
van Loon "Pathogenesis-related proteins," *Plant Molecular Biology* 4:111-116 (1985).
Vance et al. "RNA Silencing in Plants—Defense and Counterdefense," *Science* 292:2277-2280 (2001).

(56) References Cited

OTHER PUBLICATIONS

Vasil, I.K. "Milestones in crop biotechnology—Transgenic cassava and *Agrobacterium*-mediated transformation of maize," *nature Biotechnology* 14:702-703 (1996).
Vasil, I.K. "Molecular Improvement of cereals," *Plant Molecular Biology* 25(6):925-937 (1994).
Vaucheret et al. "The Action of ARGONAUTE1 in the miRNA pathway and its regulation by the miRNA pathway are crucial for plant development," *Genes and Development* 18:1187-1197 (2004).
Velten et al. "Isolation of a dual plant promoter fragment from the Ti plasmid of Agrobacterium tumefaciens," *EMBO Journal* 3(12):2723-2730 (1984).
Vionnet, O. "RNA silencing as a plant immune system against viruses," *Trends in Genetics* 17(4449-459 (2001) Elsevier Science Ltd.
Vlaska, J., et al. "Comparison of hCMV Immediate Early and CaMV 35S Promoters in both plant and human cells", Journal of Biotechnology 103 (2003), 197-202.
Walters et al. "Transformation and inheritance of a hygromycin phosphotransferase gene in maize plants," *Plant Molecular Biology* 18(2): 189-200 (1992).
Warner et al. "Isolation of an asparagus intracellular PR gene (AoPR1) wound-responsive promoter by the inverse polymerase chain reaction and its characterization in transgenic tobacco," *The Plant Journal* 3(2):191-201 (1993).
Weeks et al. "Rapid production of multiple independent lines of fertile transgenic wheat (*Triticum aestivum*)," *Plant Physiology* 102;1077-1084.
Weising "Foreign Genes in Plants: Transfer, Structure, Expression, and Applications," *Annual Review of Genetics* 22:421-477 (1988).
Yamamoto et al. "Light-responsive elements of the tobacco PSI-D gene are located both upstream and within the transcribed region," *The Plant Journal* 12(2):255-265 (1997).
Yamamoto et al. "The Promoter of a Pine Photosynthetic Gene Allows Expression of a β-Glucuronidase Reporter Gene in Transgenic Rice Plants in a Light-Independent but Tissue-Specific Manner," *Plant & Cell Physiology* 35(5):773-778 (1994).
Zamore, P.D. "RNA interference: listening to the sound of silence," *Nature Structural Biology* 8(9):746-750 (2001).
Zeng et al. "Both Natural and Designed Micro RNAs Can Inhibit the Expression of Cognate mRNAs When Expressed in Human Cells," *Molecular Cell* 9:1327-1333 (2002) Cell Press, USA.
Zhang et al. "Transgenic rice plants produced by electroporation-mediated plasmid uptake into protoplasts," *Plant Cell Reports* 7(6):379-384 (1988).
Zhang, B. & Singh, K.B. "ocs element promoter sequences are activated by auxin and salicylic acid in Arabidopsis," *Proceedings of the National Academy of Sciences of the United States of America* 91(7):2507-2511 (1994).

* cited by examiner

COMPOSITIONS AND METHODS FOR THE MODULATION OF GENE EXPRESSION IN PLANTS

CROSS-REFERENCE TO RELATED APPLICATIONS

This application is a divisional application of U.S. patent application Ser. No. 10/623,930, which claims the benefit of U.S. Provisional Application No. 60/397,487, filed Jul. 19, 2002, which is hereby incorporated herein in its entirety by reference.

FEDERALLY SPONSORED RESEARCH OR DEVELOPMENT

The research underlying this invention was supported in part with funds from National Institutes of Health grant R-02-0927 and USDA grant 200113531909848. The United States Government may have an interest in the subject matter of the invention.

FIELD OF THE INVENTION

The invention relates to compositions and methods for modulating gene expression in plants.

BACKGROUND OF THE INVENTION

Gene transfer is also being utilized to modify the quality of harvested products to maximize their use as food or industrial raw material. In the same manner, attempts to alter the amino acid composition of storage proteins to increase their nutritional value have been reported. These efforts have been met with mixed results.

Transgenic plants are also suitable for producing peptides and proteins used as pharmaceuticals, such as enkephalins, human serum albumins, or interferons. The production in transgenic plants of vaccines for use against various illnesses is being considered to reduce production costs. Additionally, transgenic plants can be engineered to produce a wide array of metabolites. Transgenic plants have been used to produce a variety of metabolites including biodegradable plastics know as polyhydroxyalkanoates, various oils that are useful for both human consumption and industrial purposes and carbohydrates.

Many factors affect gene expression in plants and other eukaryotic organisms. Recently, small RNAs, 21-26 nucleotides, have emerged as important regulators of eukaryotic gene expression. The known small regulatory RNAs fall into two basic classes. One class of small RNAs is the short interfering RNAs (siRNAs). These play essential roles in RNA silencing, a sequence-specific RNA degradation process that is triggered by double-stranded RNA (dsRNA) (see Vance and Vaucheret (2001) Science 292:2277-2280, and Zamore (2001) Nat Struct Biol 8:746-750 for recent reviews on RNA silencing in plants and animals, respectively), RNA silencing plays a natural role in defense against foreign nucleic acids including virus resistance in plants and control of transposons in a number of organisms. siRNAs are double-stranded with small 3' overhangs and derive from longer dsRNAs that induce silencing. They serve as guides to direct destruction of target RNAs and have been implicated as primers in the amplification of dsRNA via the activity of a cellular RNA dependent RNA polymerase. In plants, si-like RNAs have also been associated with dsRNA-induced transcriptional gene silencing (TGS), a process in which dsRNA with homology to promoter regions triggers DNA methylation and inhibits transcription. The TGS-associated small RNAs, unlike true siRNAs, are not involved in RNA degradation.

The second known class of small RNAs is the small temporal RNAs (stRNAs), lin-4 and let-7, that control certain developmental switches in C. elegans. The stRNAs are single-stranded, although they derive from larger precursor RNAs that are partially double-stranded. StRNAs are also functionally different from siRNAs: they interact with the 3'-untranslated end of target mRNA and inhibit translation rather than mediating RNA degradation. Unlike siRNAs, the stRNAs are only partially complementary to their target mRNAs. Remarkably, hundreds of new stRNA-like small RNAs termed microRNAs (miRNAs have been discovered in worms, flies, humans, and plants and miRNAs are likely to be discovered in other organisms as well. Like stRNAs, the miRNAs are single-stranded, and their accumulation is developmentally regulated. They derive from partially double-stranded precursor RNAs that are transcribed from genes that do not encode protein. Like stRNAs (and unlike siRNAs involved in RNA silencing), most of the miRNAs lack complete complementarity to any putative target mRNA. Although their functions are, as yet, not known, it is hypothesized that they regulate gene expression during development, perhaps at the level of development. However, given the vast numbers of these small regulatory RNAs, it is likely that they are functionally more diverse and regulate gene expression at more than one level.

SUMMARY OF THE INVENTION

Compositions and methods for modulating nucleotide sequence expression, particularly for modulating gene expression in plants, are provided. The compositions comprise precursor RNA constructs for the expression of an RNA precursor. The precursor RNA construct comprises a promoter that is expressed in a plant cell driving the expression of a precursor RNA having a microRNA. The RNA precursor is cleaved in a plant cell to form small temporal RNAs or microRNAs (miRNAs). MicroRNAs (miRNAs) are small regulatory RNAs that control gene expression. The miRNA is complementary or partially complementary to a portion of a target gene or nucleotide sequence and function to modulate expression of the target sequence or gene. In this manner, the RNA precursor construct can be designed to modulate expression of any nucleotide sequence of interest, either an endogenous plant gene or alternatively a transgene. The RNA precursor is designed to produce a transcript that is processed via the miRNA pathway to produce an miRNA complementary to a portion of RNA, the target RNA, that corresponds to the target gene. The miRNA modulates the expression of the target gene. While not bound by any mechanism of action, the miRNA may function to alter the production, processing, stability, or translation of the target RNA and thereby alter the expression of the product of the target RNA.

The precursor RNA constructs may be used in combination with modulators to enhance the effect on gene expression. Modulators are proteins of the invention alter the level of at least one miRNA in a plant cell, including, but not limited to plant and viral proteins that are known to alter RNA silencing. Expression of a modulator in the presence of the precursor RNA alters the accumulation of miRNAs and thus enhances the regulatory capabilities of miRNAs. In this manner, a plant expressing both the precursor RNA and a modulator can be constructed to modulate expression of a target gene.

A third embodiment of the invention comprises the use of a modulator to control gene expression via the siRNA and the miRNA pathway. The siRNA pathway involves RNA silencing through the accumulation of short interfering RNAs (siRNAs). These siRNAs incorporate into a silencing complex and guide sequence-specific RNA degradation. Any mRNA with sequence relatedness to the siRNA is targeted and destroyed, effectively silencing the gene. In this embodiment, the plant modulators of the invention interfere with the accumulation of siRNAs and prevent RNA silencing, providing for increased expression of the unsilenced sequence. In this manner, modulators have been used to suppress silencing of a gene or sequence of interest. Modulators have additionally been used in combination with amplicons to increase the expression of a target gene. An amplicon comprises a targeting sequence corresponding to the gene of interest, the target gene, and directs gene silencing of a sequence having homology to the targeting sequence. The amplicon may optionally comprise a promoter and a sequence that corresponds to at least a part of a viral genome. In this embodiment, the modulator can be used to enhance the regulatory effect of an miRNA and at the same time enhance expression of an amplicon silenced gene. In this embodiment, a plant expresses a modulator, a precursor RNA having miRNA corresponding to a first target sequence, and an amplicon comprising a targeting sequence corresponding to a second target sequence. The plant will demonstrate enhanced expression of the second target sequence and modified expression of the first target sequence.

It is recognized that a variety of promoters may be utilized in the constructs of the invention depending on the desired outcome. Tissue-preferred promoters, inducible promoters, developmental promoters, constitutive promoters can be used to direct expression of the first target sequence, the second target sequence or the modulator sequence in the plant.

DETAILED DESCRIPTION OF THE INVENTION

Figure 1:
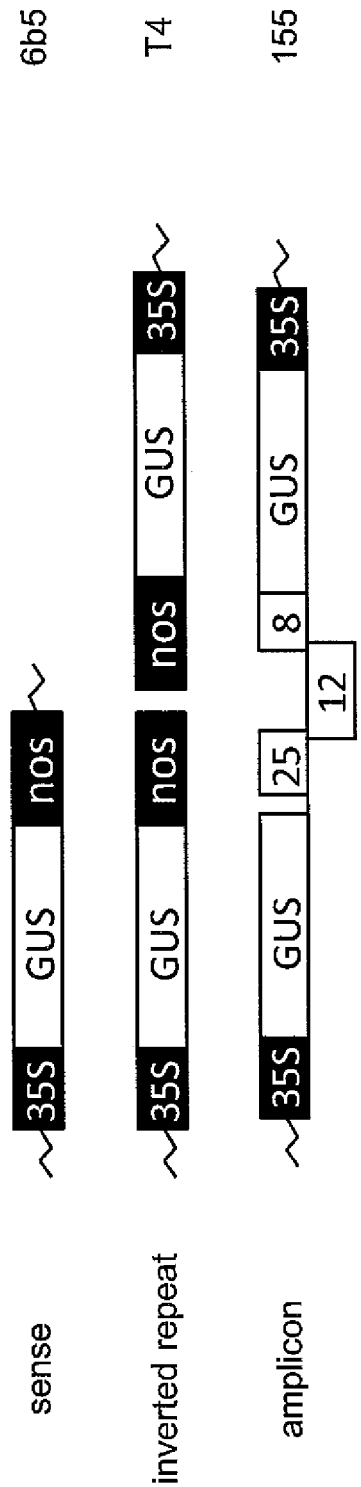
FIG. 1 is a diagram of the transgene loci in lines 6b5, T4 and 155 as predicted by DNA blot analysis. 35S indicates the position of the cauliflower mosaic virus (CaMV) 35S promoter, and nos indicates the position of the nopaline synthase terminator. Arrows indicate the direction of transcription in line T4 based on the predicted arrangement of the 35S promoters (Hobbs et al. (1990) *Plant Mol Biol* 15:851-864). The amplicon transgene in line 155 encodes a potato virus X (PVX) complementary DNA in which the coat protein gene is replaced by the GUS locus. The PVX viral open reading frames (ORFs) encode RNA-dependent RNA polymerase (RdRp), and three movement proteins, p25 (25), p12 (12), and p8 (8) (Angell and Baulcombe (1997) *Embo J* 16:3675-3684).
Figure 2:
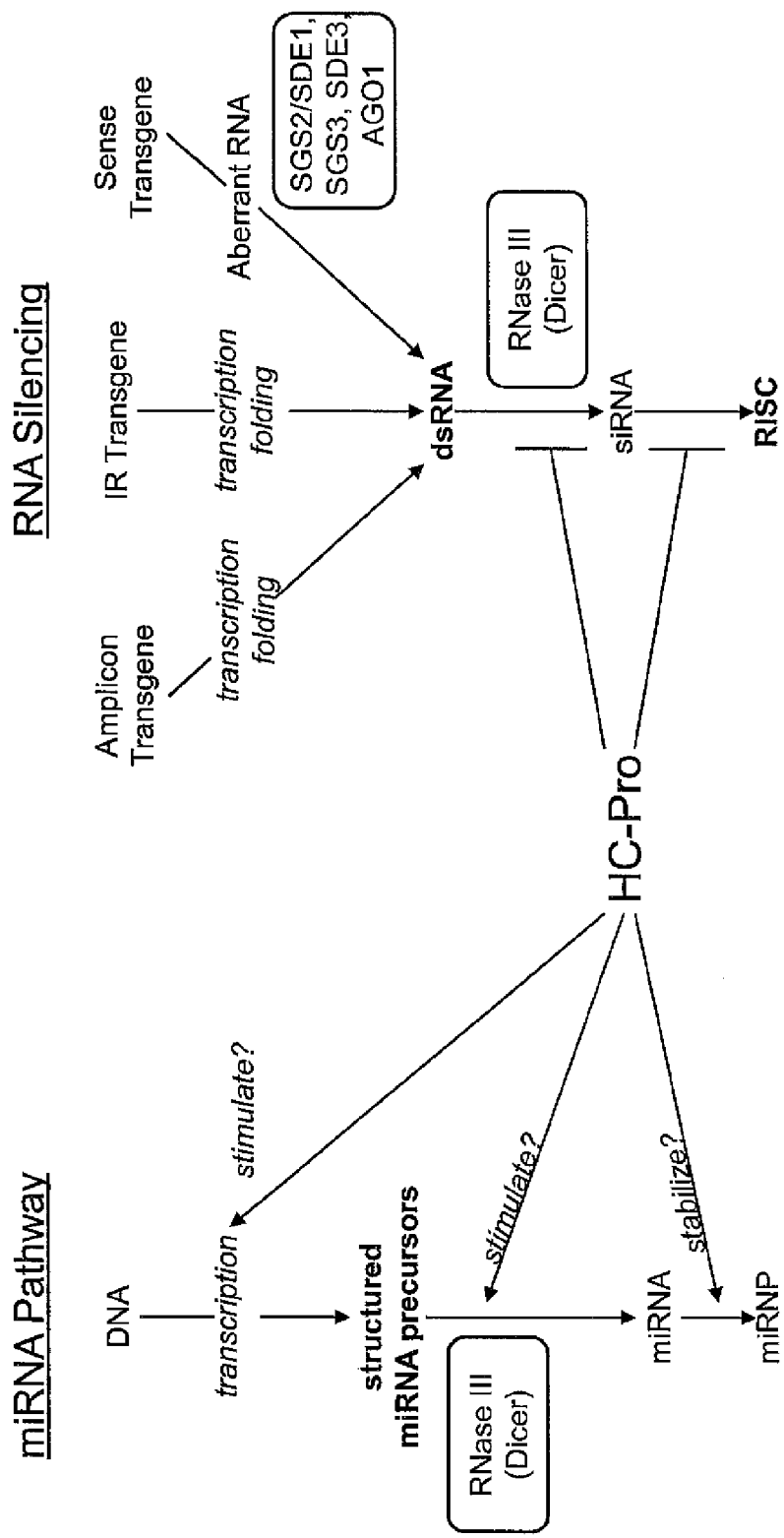
FIG. 2 is a schematic illustration of proposed RNA silencing and miRNA biogenesis pathways showing steps that could be differentially regulated by HC-Pro.

Compositions and methods for modulating target sequences in a plant are provided. The target sequences may be endogenous or exogenous plant sequences. By "endogenous" is intended that the sequences are natively present in the plant genome. "Exogenous" sequences are those sequences that are not natively present in the plant. In one aspect of the invention target sequences are modulated via the microRNA (miRNA) pathway or alterations of this pathway. MicroRNAs (miRNAs) are small regulatory RNAs that control gene expression. miRNAs bind to regions of target RNAs and inhibit their translation (thereby interfering with production of the protein encoded by the target mRNA). Thus, miRNAs of the invention will be complementary to the target gene or sequence of interest. The miRNA can be designed to be complementary to any region of the target sequence RNA including the 3' untranslated region, coding region, etc. miRNAs are processed from highly structured RNA precursors that are processed by the action of a ribonuclease III termed DICER. While the mechanism of action of these miRNAs is currently unknown, they function to regulate expression of the target gene. In this manner, the pathway that produces miRNAs can be manipulated to control regulation of specific target genes.

In this embodiment, a precursor RNA construct is designed to produce a transcript that would be processed via the miRNA pathway to produce an miRNA complementary to a target RNA, an RNA corresponding or transcribed by the target sequence. While not bound by any mechanism of action, the miRNAs alter the production, processing, stability, or translation of the target RNA and thereby alter the expression of the protein product of the targeted RNA. The miRNAs of the invention will be complementary or substantially complementary to a target RNA that corresponds to the target gene of interest. The miRNA will generally be small molecules comprising about 15 to about 30 nucleotides, about 20 to about 28 nucleotides, more specifically about 21-24 nucleotides. Generally the miRNA will be completely complementary to the target RNA, however, mismatches may be tolerated. Generally from 1-about 6 mismatches may occur, more specifically about 2-3 mismatched nucleotides may be included in the miRNA. While the mismatched nucleotides may occur throughout the miRNA sequence, preferably, they are located near the center of the molecule. In this manner, an miRNA sequence can be designed to modulate the expression of any target sequence. The miRNA is expressed as part of a precursor RNA construct. Such precursor RNA molecules are known in the art. See, for example, Reinhart et al. (2002) *Genes & Development* 16:1616-1626 and Llave et al. (2002) *Plant Cell* 14:1605-1619, herein incorporated by reference. As noted above, once the precursor RNA construct is expressed in the plant cell, it is processed to produce the miRNAs.

The regulation of a gene via miRNA can be used in combination with a modulator. Such modulators include, but are not limited to, viral (or cellular) proteins that regulate miRNA accumulation. The modulators of the invention are capable of altering the levels of at least one miRNA in a plant. For example, HC-Pro, a viral suppressor of RNA silencing, enhances the accumulation of endogenous miRNAs. Thus, the modulators of the invention can be used in combination with the RNA precursor constructs of the invention to enhance the regulatory capabilities of miRNA that correspond to target sequences of interest.

Modulators of the invention may regulate the miRNA pathway only, or like HC-Pro, may participate in both the miRNA and the siRNA pathways. Modulators of the siRNA pathway have been previously shown to suppress RNA silencing and thereby boost expression of genes that have been targeted by the silencing mechanism, such as, example, HC-Pro. RNA silencing involves the accumulation of short interfering RNAs (siRNAs) that incorporate into a silencing complex and guide sequence-specific RNA degradation. Any mRNA with sequence relatedness to the siRNAs is targeted and destroyed, resulting in failure to produce the encoded protein (and thus effectively silencing the gene). Modulators of the invention interfere with the accumulation of siRNAs and thereby prevent RNA silencing, allowing the targeted gene to be expressed.

In the present invention, a modulator is used to alter regulation of the miRNA pathway. The modulator may work to enhance the accumulation of small regulatory RNAs called miRNAs. Though both siRNAs and miRNAs control gene expression, the biogenesis of these two classes of small RNAs is different and the modulators of the invention may affect their accumulation in different ways.

It is further recognized that gene expression in a plant expressing a modulator that acts on both pathways may be manipulated using both the miRNA and the siRNA pathways. That is, the plant expressing a modulator could be further designed to express a precursor RNA construct of interest that modulates the expression of a first target sequence via the miRNA pathway and to express an amplicon (wherein the amplicon comprises at least a promoter that drives expression in a plant cell operably linked to a targeting sequence that corresponds to a second target sequence of interest) that modulates the expression of a second target sequence via the siRNA pathway. The second target sequence would be highly expressed and the expression of the first target sequence would be altered or modified. Expression of the first target sequence controlled via the miRNA pathway could be effectively silenced (their expression reduced) or alternatively increased. The modulators of the invention may act as both an enhancer and a suppressor of gene expression depending on the circumstances.

The methods of the invention involve modulating the expression of one, two, or more target nucleotide sequences in a plant are provided. That is, the expression of a target nucleotide sequence of interest may be increased or decreased. By "increased expression" is intended that expression of the target nucleotide sequence is increased over expression observed in conventional transgenic lines for heterologous genes and over endogenous levels of expression for homologous genes. Heterologous or exogenous genes comprise genes that do not occur in the plant of interest in its native state. Homologous or endogenous genes are those that are natively present in the plant genome. Generally, expression of the target sequence is substantially increased. That is expression is increased at least about 25%-50%, preferably about 50%-100%, more preferably about 100%, 200% and greater.

By "decreased expression" is intended is intended that expression of the target nucleotide sequence is decreased below expression observed in conventional transgenic lines for heterologous genes and below endogenous levels of expression for homologous genes. Generally, expression of the target nucleotide sequence of interest is substantially decreased. That is expression is decreased at least about 25%-50%, preferably about 50%-100%, more preferably about 100%, 200% and greater.

The invention relates to the regulation of gene expression via mechanisms that involve small regulatory RNAs, particularly siRNAs and miRNAs. "Gene silencing", which is also known as "RNA silencing", is generally used to refer to suppression of expression of a gene and involves siRNAs. The degree of reduction may be partial or total reduction in production of the encoded gene product. Therefore, the term should not be taken to require complete "silencing" of expression. Methods for gene silencing are known in the art and include co-suppression and antisense suppression. See, for example, PCT/GB 98/00442 and PCT/GB 98/02862, herein incorporated by reference.

The methods of the invention relates to modulating the expression of one, two, or more target nucleotide sequences or genes in plants. The target nucleotide sequences may be endogenous or exogenous in origin. By "modulate expression of a target gene" is intended that the expression of the target gene is increased or decreased relative to the expression level in a plant that has not been altered by the methods described herein. Expression levels may be assessed by determining the level of a gene product by any method known in the art including, but not limited to determining the levels of the RNA and protein encoded by a particular target gene. For genes that encode proteins, expression levels may determined, for example, by quantifying the amount of the protein present in plant cells, or in a plant or any portion thereof. Alternatively, it desired target gene encodes a protein that has a known measurable activity, then activity levels may be measured to assess expression levels.

The target nucleotide sequence comprises any nucleotide sequence or gene of interest, including genes, regulatory sequences, etc. Genes of interest include those encoding agronomic traits, insect resistance, disease resistance, herbicide resistance, sterility, grain characteristics, and the like. The genes may be involved in metabolism of oil, starch, carbohydrates, nutrients, etc. Genes or traits of interest include, but are not limited to, environmental- or stress-related traits, disease-related traits, and traits affecting agronomic performance. Target sequences also include genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

The compositions comprise precursor RNA constructs for the expression of an RNA precursor. The precursor RNA construct comprises a promoter that is expressed in a plant cell driving the expression of a nucleotide sequence that encodes the precursor RNA having a microRNA. The RNA precursor is cleaved in a plant cell to form miRNAs. The miRNA is complementary to a portion of a target gene or nucleotide sequence and function to modulate expression of the target sequence or gene. The precursor RNA constructs are designed to direct the expression in the plant an RNA precursor that has an miRNA that is complementary to a portion of a target nucleotide sequence. Such precursor RNAs, their respective miRNAs and the genes that encode them are known in the art and have been identified in plants. See, Reinhart et al. (2002) *Genes & Development* 16:1616-1626 and Llave et al. (2002) *Plant Cell* 14:1605-1619. The nucleotide sequence that encodes the precursor RNA that comprises an miRNA region that is complementary to a portion of the target gene. The regions which flank the miRNA region are selected from the sequences known in the art for miRNA precursors, particularly plant miRNA precursors, more particularly those plant miRNA precursors disclosed by Reinhart et al. (2002) *Genes & Development* 16:1616-1626 and Llave et al. (2002) *Plant Cell* 14:1605-1619. In general, an RNA precursor is constructed by obtaining the sequence of known RNA precursor for an miRNA and replacing the miRNA sequences therein with the miRNA sequences directed to the target gene of interest. Methods for constructing precursor miRNAs and miRNAs that can be used to alter the expression of specific target genes are known in the art. See, for example, McManus et al. (2002) *RNA* 8:842-850. Alternatively, precursor miRNAs can be isolated by methods known in the art (Reinhart et al. (2002) *Genes & Development* 16:1616-1626 and Llave et al. (2002) *Plant Cell* 14:1605-1619).

For a target gene of interest, the miRNA of the invention is complementary or partially complementary to a region of the target gene. That is the miRNA comprises a region that is completely complementary to a region of the target gene, or the miRNA comprises a region that is partially complementary to a region of the target gene. By partially complementary, it is intended the corresponding regions of the target gene and the miRNA have one, two, three, or more mismatched bases. It is recognized in the art that miRNAs may not be completely complementary to the region of a target gene.

The miRNAs of the invention comprise a region of that is complementary or partially complementary to a region of the target gene. While the invention does not depend on miRNAs of a particular size, the miRNAs known in the art typically comprise between about 15 and 30 nucleotides.

For purposes of the invention, a nucleotide sequence encoding a modulator is utilized in combination with a nucleotide sequence encoding a precursor miRNA. The modulator is capable of modulating the level of at least one miRNA in a plant cell, and may also be capable of suppressing co-suppression in plants, such as, for example, the silencing of an inverted repeat transgene, and amplicon transgene or a sense transgene. See, for example, PCT/US 98/06075, herein incorporated by reference. As discussed above, miRNAs are involved in regulating gene expressions in organisms. In fact, synthetic miRNA can either be transfected into cells or expressed in the cell under the control of an RNA polymerase III promoter and cause the decreased expression of a specific target nucleotide sequence (McManus et al. (2002) *RNA* 8:842-850, herein incorporated by reference). While the instant invention does not depend on a particular biological mechanism for miRNAs modulating gene expression, such miRNAs are not believed to be involved in RNA silencing, which involves a sequence-specific RNA degradation process and siRNAs that is triggered by double-stranded RNA (dsRNA).

As is described in detail below, a modulator of the invention, HC-Pro is known to cause the suppression of RNA silencing of inverted repeat, amplicon, and sense transgenes in plants and that this suppression is correlated with a decrease in the levels of siRNA in the plants. Furthermore, it has been discovered that HC-Pro is also capable of causing at the same time in these plants increase in the levels of specific miRNAs therein.

Modulators of the invention include, but are not limited to, any protein that is capable modulating the levels of one or more miRNAs in a plant cell. Such proteins include, but are not limited to eukaryotic and viral proteins, including the plant protein rg-CaM. See, Anandalakshmi et al. (2000) *Science* 290:142-144. Such modulators include, but are not limited to, viral proteins that are know to act as suppressors of gene silencing in plants (viral suppressors). Such viral suppressors may be selected from the 5'-proximal region of potyviral genomes, such as from tobacco etch potyviral (TEV), potato virus Y and the like. The skilled artisan will appreciate that the 5' proximal regions are also termed P1/HC-Pro sequence. The P1/HC-Pro sequence has been shown to interfere with a general antiviral system in plants, thereby permitting viruses to accumulate beyond the normal host-mediated limits. The sequence may act as a suppressor of transgene-induced, amplicon induced and virus-induced gene silencing. Other modulators or viral suppressors include the 2b protein of cucumber mosaic virus (CMV), HC-Pro of potato virus Y (PVY), other virally encoded proteins, and the like. It is recognized that sequences from other organisms, including for example, other plants, animals, and viruses, may also act as modulators. Such modulators may assayed for the activity of modulating the levels of one or more miRNAs in a plant as described below for HC-Pro. Such modulators may also be assayed for the suppression of gene silencing by the methods described below and in Brigneti et al. (1998) *EMBO Journal* 17:6739-6746, herein incorporated by reference. Theses methods utilize plants exhibiting post-transcriptional gene silencing of a marker gene, such as, for example, green fluorescent protein. Such plants are infected with a potyvirus or with CMV. Silenced plants were also infected with potato virus X (PVX) and with chimeric constructs carrying coding sequences from PVY and CMV. Expression of sequences comprising a modulator would result in transgene expression of the marker protein. Additionally, the modulators will cause an increase in the level of one or more miRNAs in the plant.

Variants or sequences having substantial identity or homology with the modulator molecules may be utilized in the practices of the invention. That is, the modulator may be modified yet still retain the ability to modulate the level of one or more miRNAs in a plant or plant cell, and, in certain embodiments of the invention, the modulator may also retain the ability to act as a suppressor of post-transcriptional gene silencing. Generally, the modulator will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the native modulator sequence as determined by sequence alignment programs described elsewhere herein using default parameters.

Sequence relationships between two or more nucleic acids or polynucleotides are generally defined as sequence identity, percentage of sequence identity, and substantial identity. See, for example, "Pedestrian Guide to Analyzing Sequence Data Bases" at www.embl-heidelberg.de/~schneide/paper/springer96/springer.html. In determining sequence identity, a "reference sequence" is used as a basis for sequence comparison. The reference sequence may be a subset or the entirety of a specified sequence. That is, the reference sequence may be a full-length gene sequence or a segment of the gene sequence.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, PASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244; Higgins et al. (1989) *CABIOS* 5:151-153; Corpet et al. (1988) *Nucleic Acids Res.* 16:10881-90; Huang et al. (1992) *CABIOS* 8:155-65; and Pearson et al, (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

"Sequence identity" or "identity" in the context of nucleic acid or polypeptide sequences refers to the nucleic acid bases or residues in the two sequences that are the same when aligned for maximum correspondence over a specified comparison window. "Percentage of sequence identity" refers to the value determined by comparing two optimally aligned sequences over a comparison window, wherein the portion of the polynucleotide sequence in the comparison window may comprise additions or deletions as compared to the reference window for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Polynucleotide sequences having "substantial identity" are those sequences having at least about 50%, 60% sequence identity, generally 70% sequence identity, preferably at least 80%, more preferably at least 90%, and most preferably at least 95%, compared to a reference sequence using one of the alignment programs described above. Preferably sequence identity is determined using the default parameters determined by the program. Substantial identity of amino acid sequences generally means sequence identity of at least 50%, more preferably at least 70%, 80%, 90%, and most preferably at least 95%.

Nucleotide sequences are generally substantially identical if the two molecules hybridize to each other under stringent conditions. Generally, stringent conditions are selected to be about 5° C. lower than the thermal melting point for the specific sequence at a defined ionic strength and pH. Nucleic acid molecules that do not hybridize to each other under stringent conditions may still be substantially identical if the polypeptides they encode are substantially identical. This occurs when a copy of a nucleic acid is created using the maximum codon degeneracy permitted by the genetic code.

As noted, hybridization of sequences may be carried out under stringent conditions. By "stringent conditions" is intended conditions under which a probe will hybridize to its target sequence to a detectably greater degree than to other sequences. Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 1% SDS (sodium dodecyl sulphate) at 37° C., and a wash in 1× to 2×SSC (20×SSC=3.0 M NaCl/0.3 M trisodium citrate) at 50 to 55° C. It is recognized that the temperature salt and wash conditions may be altered to increase or decrease stringency conditions. The duration of hybridization is generally less than about 24 hours, usually about 4 to about 12 hours. For the post-hybridization washes, the critical factors are the ionic strength and temperature of the final wash solution. See, Meinkoth and Wahl (1984) *Anal. Biochem.* 138:267-284.

As indicated, fragments and variants of the nucleotide sequences of the invention are encompassed herein. By "fragment" is intended a portion of the nucleotide sequence. Fragments of the modulator sequence will generally retain the biological activity of the native suppressor protein. Alternatively, fragments of the targeting sequence may or may not retain biological activity. Such targeting sequences may be useful as hybridization probes, as antisense constructs, or as co-suppression sequences. Thus, fragments of a nucleotide sequence may range from at least about 20 nucleotides, about 50 nucleotides, about 100 nucleotides, and up to the full-length nucleotide sequence of the invention.

By "variants" is intended substantially similar sequences. For nucleotide sequences, conservative variants include those sequences that because of the degeneracy of the genetic code, encode the amino acid sequence of the modulator of the invention. Variant nucleotide sequences include synthetically derived sequences, such as those generated, for example, using site-directed mutagenesis. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

Variant modulator proteins may also be utilized. By "variant" protein is intended a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function. Variant proteins encompassed by the present invention are biologically active, that is they continue to possess the desired biological activity of the native protein, that is, modulator activity as described herein. Biologically active variants of a native modulator protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The target sequence also includes fragments and variants of proteins or regulator sequences. The target proteins of the invention may include those that are altered in various ways including amino acid substitutions, deletions, truncations, and insertions. Methods for such manipulation are generally known in the art. See, for example, Kunkel (1985) *Proc. Natl. Acad. Sci. USA* 82:488-492; Kunkel et al. (1987) *Methods and Enzymol.* 154:367-382; and the references cited therein.

The methods of the invention are useful in any situation where increased or decreased expression of a nucleotide sequence is desired. Thus, the methods are useful for increasing or decreasing the expression of endogenous as well as exogenous sequences. For example, for exogenous sequences, the modulator sequence can be used to enhance expression of genes silenced using transgene-induced gene silencing. Therefore, the target sequence may be any nucleotide sequence of interest. In one embodiment, the methods can be used to produce peptides or proteins that cannot effectively be commercially produced by existing gene expression systems. For example, some proteins cannot be expressed in mammalian systems because the protein interferes with cell viability, cell proliferation, cellular differentiation, or protein assembly in mammalian cells. Such proteins include, but are not limited to, retinoblastoma protein, p53, angiostatin, and leptin. Likewise, the methods of the invention can be used to produce mammalian regulatory proteins. Other sequences of interest include proteins, hormones, growth factors, cytokines, preferably insulin, growth hormone, particularly human growth hormone, interferon, particularly α-interferon, β-glucocerebrosidase, serum albumin, particularly human serum albumin, hemoglobin, collagen, etc. In such instances, generally, the modulator sequence will be operably linked to a constitutive promoter.

In another embodiment, the methods of the invention can be used to produce transgenic seed and seed products. In this manner, the nucleotide sequence encoding the RNA precursor and/of the modulator can be operably linked with a seed-preferred, or endosperm promoter. Such seed proteins of interest include, but are not limited to, starches, storage proteins, proteins with enhanced nutritional value, specialty oils, carotenoids, etc.

Generally, the methods of the invention can be used to increase or decrease the expression of any gene or sequence of interest including therapeutic or immunogenic peptides and proteins, nucleic acids for controlling gene expression, genes to reproduce enzymatic pathways for chemical synthesis, genes to shunt an enzymatic pathway for enhanced expression of a particular intermediate or final product, industrial processes, and the like.

It is recognized that the methods of the invention can be used for increased or decreased expression of one, two or more target nucleotide sequences in transformed plants, plant cells and tissues, seed, and the like. Thus, in some embodiments, it may be beneficial to provide the methods in a plant culture system for production of metabolites, peptides or proteins of interest.

As discussed, a number of promoters can be used in the practice of the invention. The promoters can be selected based on the desired outcome. Generally, the RNA precursor nucleotide sequence and the modulator sequences can be combined with promoters of choice to alter gene expression if the target sequences in the tissue or organ of choice. Thus, the RNA precursor nucleotide sequence or modulator nucleotide sequence can be combined with constitutive, tissue-preferred, inducible, developmental, or other promoters for expression in plants depending upon the desired outcome.

Constitutive promoters include, for example, CaMV 35S promoter (Odell et al. (1985) *Nature* 313:810-812); rice actin (McElroy et al. (1990) *Plant Cell* 2163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680; 5,268,463; and 5,608,142.

A number of inducible promoters are known in the art. For resistance genes, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. Of particular interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhaug et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386; Cordero et al. (1992) *Physiol. Mol. Plant Path.* 41:189-200; and the references cited therein.

Additionally, as pathogens find entry into plants through wounds or insect damage, a wound-inducible promoter may be used in the DNA constructs of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al, (1991) *Mol. Gen. Genet.* 227:229-237, and U.S. Pat. Nos. 5,814,618 and 5,789,156), herein incorporated by reference.

Where enhanced expression in particular tissues is desired, tissue-preferred promoters can be utilized. Tissue-preferred promoters include those described by Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

Leaf-preferred promoters include, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature. See, for example, Hire et al. (1992) *Plant Mol. Biol.* 20(2): 207-218 (soybean root-preferred glutamine synthetase gene); Keller and Baumgartner (1991) *Plant Cell* 3(10):1051-1061 (root-preferred control element in the GRP 1.8 gene of French bean); Sanger et al. (1990) *Plant Mol. Biol.* 14(3):433-443 (root-preferred promoter of the mannopine synthase (MAS) gene of *Agrobacterium tumefaciens*); Miao et al. (1991) *Plant Cell* 3(1):11-22 (full-length cDNA clone encoding cytosolic glutamine synthetase (GS), which is expressed in roots and root nodules of soybean). Bogusz et al. (1990) *Plant Cell* 2(7):633-641 (root-preferred promoters from hemoglobin genes from the nitrogen-fixing nonlegume *Parasponia andersonii* and the related non-nitrogen-fixing nonlegume *Trema tomentosa*). Leach and Aoyagi (1991) *Plant Science* (Limerick) 79(1):69-76 (rolC and rolD root-inducing genes of *Agrobacterium rhizogenes*); Teeri et al. (1989) *EMBO J.* 8(2):343-350) (octopine synthase and TR2' gene); (VfENOD-GRP3 gene promoter); Kuster et al. (1995) *Plant Mol. Biol.* 29(4):759-772 and Capana et al. (1994) *Plant Mol. Biol.* 25(4):681-691 rolB promoter. See also U.S. Pat. Nos. 5,837,876; 5,750,386; 5,633,363; 5,459,252; 5,401,836; 5,110,732; and 5,023,179.

Anther or pollen-preferred promoters may be used to create male sterile plants. While either the RNA precursor nucleotide sequence or the modulator nucleotide sequence may be operably linked to such promoters, it may be preferred to express both the modulator and the targeting sequence with an anther preferred or pollen preferred promoter to prevent oven low expression of the toxin in other tissues of the plant.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); celA (cellulose synthase); gama-zein; Glob-1; bean β-phaseolin; β-conglyeinin; soybean lectin; cruciferin; maize 15 kDa zein; 22 kDa zein; 27 kDa zein; g-zein; waxy; shrunken 1; shrunken 2; globulin 1, etc.

The RNA precursor and modulator sequences of the invention may be provided in nucleotide sequence constructs or expression cassettes for expression in the plant of interest. The cassette will include 5' and 3' regulatory sequences operably linked to an miRNA nucleotide sequence or modulator nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The expression cassette may additionally contain at least one additional gene to be cotransformed into the organism. Alternatively, the additional gene(s) can be provided on multiple expression cassettes.

Such an expression cassette is provided with a plurality of restriction sites for insertion of the sequences of the invention to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) for enhanced expression may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When desired, the sequence is modified to avoid predicted hairpin secondary mRNA structures. However, it is recognized that in the case of nucleotide sequences encoding the miRNA precursors, one or more hairpin and other secondary structures may be desired for proper processing of the precursor into an mature miRNA and/or for the functional activity of the miRNA in gene silencing.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al, (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The invention involves plant cells and plants that comprise two or more nucleotide sequence constructs. Any means for producing a plant comprising the nucleotide sequence constructs described herein are encompassed by the present invention. For example, a nucleotide sequence encoding the modulator can be used to transform a plant at the same time as the nucleotide sequence encoding the precursor RNA. The nucleotide sequence encoding the precursor mRNA can be introduced into a plant that has already been transformed with the modulator nucleotide sequence. Alternatively, transformed plants, one expressing the modulator and one expressing the RNA precursor, can be crossed to bring the genes together in the same plant. Likewise, viral vectors may be used to express gene products by various methods generally known in the art. Suitable plant viral vectors for expressing genes should be self-replicating, capable of systemic infection in a host, and stable. Additionally, the viruses should be capable of containing the nucleic acid sequences that are foreign to the native virus forming the vector. Transient expression systems may also be used.

Plants transformed with a nucleotide sequence construct of the invention may be produced by standard techniques known in the art for the genetic manipulation of plants. DNA can be transformed into plant cells using any suitable technology, such as a disarmed Ti-plasmid vector carried by *Agrobacterium* exploiting its natural gene transferability (BP-A-270355, BP-A-0116718, *NAR* 12(22):8711-87215 (1984), Townsend et al., U.S. Pat. No. 5,563,055); particle or microprojectile bombardment (U.S. Pat. No. 5,100,792, BP-A-444882, RP-A-434616; Sanford et al., U.S. Pat. No.

4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926); microinjection (WO 92/09696, WO 94/00583, EP 331083, EP 175966, Green et al. (1987) *Plant Tissue and Cell Culture*, Academic Press, Crossway et al. (1986) *Biotechniques* 4:320-334); electroporation (EP 290395, WO 8706614, Riggs et al. (1986) *Proc. Natl. Acad. Sci. USA* 83:5602-5606; D'Halluin et al. (1992) *Plant Cell* 4:1495-1505) other forms of direct DNA uptake (DE 4005152, WO 9012096, U.S. Pat. No. 4,684,611, Paszkowski at al. (1984) *EMBO J.* 3:2717-2722); liposome-mediated DNA uptake (e.g., Freeman at al. (1984) *Plant Cell Physiol.* 29:1353); or the vortexing method (e.g., Kindle (1990) *Proc. Nat. Acad. Sci. U.S.A.* 87:1228). Physical methods for the transformation of plant cells are reviewed in Oard (1991) *Biotech. Adv.* 9:1-11. See generally, Weissinger et al. (1988) *Ann. Rev. Genet.* 22:421-477; Sanford et al. (1987) *Particulate Science and Technology* 5:27-37; Christou et al. (1988) *Plant Physiol.* 87:671-674; McCabe et al. (1988) *Bio/Technology* 6:923-926; Finer and McMullen (1991) *In Vitro Cell Dev. Biol.* 27P:175-182; Singh et al. (1998) *Theor. Appl. Genet.* 96:319-324; Datta et al. (1990) *Biotechnology* 8:736-740; Klein et al. (1988) *Proc. Natl. Acad. Sci. USA* 85:4305-4309; Klein et al. (1988) *Biotechnology* 6:559-563; Tomes, U.S. Pat. No. 5,240,855; Buising at al., U.S. Pat. Nos. 5,322,783 and 5,324,646; Klein et al. (1988) *Plant Physiol.* 91:440-444; Fromm at al. (1990) *Biotechnology* 8:833-839; Hooykaas-Van Slogteren et al. (1984) *Nature* (London) 311:763-764; Bytebier et al. (1987) *Proc. Natl. Acad. Sci. USA* 84:5345-5349; De Wet at al. (1985) in *The Experimental Manipulation of Ovule Tissues*, ed. Chapman et al. (Longman, New York), pp. 197-209; Kaeppler at al. (1990) *Plant Cell Reports* 9:415-418 and Kaeppler at al. (1992) *Theor. Appl. Genet.* 84:560-566; Li at al. (1993) *Plant Cell Reports* 12:250-255 and Christou and Ford (1995) *Annals of Botany* 75:407-413; Osjoda at al. (1996) *Nature Biotechnology* 14:745-750; all of which are herein incorporated by reference.

*Agrobacterium* transformation is widely used by those skilled in the art to transform dicotyledonous species. Recently, there has been substantial prowess towards the routine production of stable, fertile transgenic plants in almost all economically relevant monocot plants (Toriyaina at al. (1988) *Bio/Technology* 6:1072-1074; Zhang, et al. (1988) *Plant Cell Rep.* 7:379-384; Zhang at al. (1988) *Theor. Appl. Genet.* 76:835-840; Shimamoto at al. (1989) *Nature* 338:274-276; Datta at al. (1990) *Bio/Technology* 8: 736-740; Christou at al. (1991) *Bio/Technology* 9:957-962; Peng et al. (1991) International Rice Research Institute, Manila, Philippines, pp. 563-574; Cao et al. (1992) *Plant Cell Rep.* 11:585-591; Li et al. (1993) *Plant Cell Rep.* 12:250-255; Rathore et al. (1993) *Plant Mol. Biol.* 21:871-884; Fromm et al. (1990) *Bio/Technology* 8:833-839; Tomes et al. (1995) "Direct DNA Transfer into Intact Plant Cells via Microprojectile Bombardment," in. *Plant Cell, Tissue, and Organ Culture: Fundamental Methods*, ed. Gamborg and Phillips (Springer-Verlag, Berlin); D'Halluin et al. (1992) *Plant Cell* 4:1495-1505; Walters et al. (1992) *Plant Mol. Biol.* 18:189-200; Koziel et al. (1993) *Biotechnology* 11:194-200; Vasil, I. K. (1994) *Plant Mol. Biol.* 25:925-937; Weeks et al. (1993) *Plant Physiol.* 102:1077-1084; Somers et al. (1992) *Bio/Technology* 10:1589-1594; WO 92/14828). In particular, *Agrobacterium* mediated transformation is now emerging also as an highly efficient transformation method in monocots (Hiei, et al. (1994) *The Plant Journal* 6:271-282). See also, Shimamoto, K. (1994) *Current Opinion in Biotechnology* 5:158-162/Vasil, et al. (1992) *Bio/Technology* 10:667-674; Vain, et al. (1995) *Biotechnology Advances* 13(4):653-671; Vasil, et al. (1996) *Nature Biotechnology* 14:702).

Microprojectile bombardment, electroporation and direct DNA uptake are preferred where *Agrobacterium* is inefficient or ineffective. Alternatively, a combination of different techniques may be employed to enhance the efficiency of the transformation process, e.g., bombardment with *Agrobacterium*-coated microparticles (EP-A-486234) or microprojectile bombardment to induce wounding followed by co-cultivation with *Agrobacterium* (EP-A-486233).

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al. (1984) in *Cell Culture and Somatic Cell Genetics of Plants*, Vols. I, II, and III, and *Laboratory Procedures and Their Applications* (Academic Press); and Weissbach et al. (1989) *Methods For Plant Mol. Biol.*

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention there is provided a plant cell having the nucleotide sequence constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant. Plant extracts and derivatives are also provided.

The present invention may particularly be applied in plants such as natural hosts of a plant virus, including any mentioned herein, though it is an advantage of embodiments of the present invention that viruses may be used for gene silencing in plants which are not their natural hosts.

The present invention may be used for transformation of any plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthantiana*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

Preferably, plants of the present invention are crop plants (for example, cereals and pulses, maize, wheat, potatoes, tapioca, rice, sorghum, millet, cassava, barley, pea, and other root, tuber, or seed crops. Important seed crops are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations and geraniums. The present invention may be applied to tobacco, cucurbits, carrot, strawberry, sunflower, tomato, pepper, chrysanthemum, poplar, eucalyptus, and pine.

Grain plants that provide seeds of interest include oil-seed plants and leguminous plants. Seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

EXPERIMENTAL

Example 1

HC-Pro Suppression of IR- or Amplicon-Induced RNA Silencing Interferes with the Accumulation of siRNAs and Promotes Accumulation of a Novel Class of Slightly Larger RNAs RNA silencing is induced by dsRNA that is cleaved into the siRNAs that mediate sequence-specific RNA degradation. HC-Pro suppression of RNA silencing induced by the b-glucuronidase (GUS) sense transgene eliminates the accumulation of siRNAs (Elmayan and Vaucheret (1996) *Plant Journal* 9:787-797; Mallory et al. (2001) *Plant Cell* 13:571-583). To determine if HC-Pro suppression of RNA silencing in IR and amplicon transgenic lines T4 and 155 (Angell and Baulcombe (1997) *Embo J* 16:3675-3684; Hobbs et al. (1990) *Plant Mol Biol* 15:851-864) also eliminates siRNA accumulation, small RNAs were analyzed from the offspring of crosses between these lines and either a non-transformed (NT) control plant or an HC-Pro expressing line (line X-27-8; Mallory et al., 2001). The IR transgene in line T4 contains two GUS genes arranged as an inverted repeat and therefore produces GUS dsRNA via read-through transcription. The amplicon transgene in line 155 is comprised of complementary DNA encoding the potato virus X (PVX) genomic RNA in which the coat protein gene is replaced by the GUS locus. The transcript produced by the amplicon transgene is a replicating PVX vector and thus produces dsRNA replication intermediates with 2.5 homology to both PVX and GUS sequences. See, FIG. 1.

The IR- and amplicon-silenced lines, like the sense transgene-silenced line 6b5, accumulated siRNAs. The small RNAs produced in these three different lines were analyzed by high-resolution gel electrophoresis. In each case, the size of the small RNAs was very similar, ranging from 21-24 nt and comprised of two major populations, one corresponding to approximately 22 nt and the other to approximately 24 nt. The small RNAs in each of these silenced lines hybridized to probes specific to both sense-strand GUS RNA and antisense-strand GUS RNA, indicating the double stranded nature expected for siRNAs. Thus, these small RNAs have all the characteristics of bonafide siRNAs.

Examination of small RNAs isolated from sense, IR and amplicon transgene lines crossed with a line expressing HC-Pro showed that HC-Pro interfered with accumulation of the 21-24 nt siRNAs in all three of these lines. However, surprisingly, HC-Pro suppression of IR- and amplicon-induced RNA silencing resulted in accumulation of a longer species of small RNAs, approximately 25-27 nt. These 25-27 nt small RNAs accumulated to very high levels during HC-Pro suppression of amplicon-induced RNA silencing, presumably reflecting the vastly increased amount of replicating PVX-GUS RNA in this line (Mallory et al. (2002) *Nat Biotechnol* 20:622-625). Like the RNA silencing-associated small RNAs, the double stranded nature of the longer small RNAs was evidenced by hybridization with both sense-strand and antisense-strand GUS RNA probes. Thus, suppression of RNA silencing by HC-Pro eliminates siRNAs for all three types of transgenes, but in the case of IR and amplicon transgenes, a larger class of small RNAs accumulates instead. This result suggests that HC-Pro either interferes with the accumulation or processing of the double stranded small RNA precursors or alters the stability of the small RNA products.

Example 2

HC-Pro Increases the Level of miRNA Accumulation in Tobacco

HC-Pro inhibits siRNA accumulation, suggesting that HC-Pro may alter the activity of the Dicer-like RNase III responsible for siRNA production. Because miRNAs are also products of a Dicer-like RNase III in plants (Reinhart et al. (2002) *Genes & Development* 16:1616-1626), we examined the effect of HC-Pro on miRNA accumulation. Four miRNAs were chosen for these experiments. Each was identified in *Arabidopsis*, but predicted, on the basis of sequence similarity, to be highly conserved throughout the flowering plants. The expression of all four miRNAs was detected in tobacco supporting the phylogenetic conservation of the miRNAs (Reinhart et al. (2002) *Genes & Development* 16:1616-1626). Strikingly, we found that BC-Pro increased the accumulation of these miRNAs approximately 5 to 10 fold. No miRNA precursors were detected in HC-Pro-expressing or nonexpressing lines suggesting that they are rapidly processed, degraded or too large to be resolved on these gels. The increase in miRNA accumulation was independent of the silencing locus present in the plants because there was little difference in miRNA levels in 155×HC-Pro, 6b5×HC-Pro and T4×HC-Pro plant lines. Furthermore, the level of miRNA accumulation was similar in a GUS-expressing control line and a GUS-silenced line, suggesting that RNA silencing does not reduce miRNA accumulation by competing for components shared by the two pathways.

The effect of HC-Pro on accumulation of two of the miRNAs in flower, leaf and stem tissues was also analyzed. HC-Pro increased the accumulation of both miRNAs, and in some cages the increase was tissue specific. For example, HC-Pro preferentially enhances the level of miR167 accumulation in leaves as compared to stems or flowers. These data indicate that HC-Pro differentially increases the accumulation of some miRNAs in a tissue specific manner.

Example 3

Construction and Optimization of Nucleotide Sequences Encoding miRNAs

Precursors miRNA are designed to target specific messenger RNAs (mRNAs) and alter expression of the protein encoded by that mRNA by the method described hereinbelow or by any other method known in the art. The overall approach is to design an RNA transcript (the miRNA precursor) that is capable of being processed via the miRNA biogenesis pathway to produce an miRNA that is complementary to a particular target mRNA. The miRNA that is processed from this designer miRNA precursor is capable of binding to the targeted mRNA and altering the expression of the protein it encodes. The expression of the targeted protein is assayed to determine if expression of the miRNA precursor results in altered gene expression. There are three steps in implementation of the method: 1) the designer miRNA precursor is constructed and cloned into a binary vector 2) the designer miRNA is expressed in plants or plant tissues that also express the target mRNA 3) the expression of the protein encoded by the targeted mRNA is assayed. In one embodiment of the invention, the target mRNA encodes the reporter enzyme β-glucuronidase (GUS) and is constitutively expressed in transgenic Nicotiana benthamiana plants (for transient expression assays) or Arabidopsis thaliana plants (for stable transformation assays). A more detailed description of the approach follows.

Step 1. Design of the miRNA Precursor.

The initial experiments will determine the features that are required in an miRNA precursor in order to achieve appropriate processing via the miRNA pathway. The initial miRNA precursors will be designed to mimic endogenous miRNA precursors such as those reported in Llave et al. (2002) Plant Cell 14:1605-1619 and Reinhart et al. (2002) Genes & Development 16:1616-1626. These precursors are characteristically stem-loop structures in which the stem is not completely double-stranded. The single-stranded miRNA is processed from the stem of the precursor and is commonly flanked by bulges. In these studies, a number of miRNA precursors will be designed that have all the features of an endogenous miRNA precursor, but the position of the endogenous miRNA will be replaced with that of the desired miRNA (one that is complementary or partly complementary to the desired target mRNA). For example, the designer miRNA precursor will contain a loop chosen from an endogenous miRNA precursor. The desired miRNA will be a sequence that is complementary to the GUS mRNA (initially the chosen miRNA sequence is complementary to either the 3'-untranslated region or the coding region, but limited to those regions) and will be inserted in a position analogous to an authentic miRNA within the precursor. Bulges will be included and these too will be taken from the context of the endogenous precursor.

Step 2. Express the Designer miRNA Precursor in Plant Tissues that Also Express the Target mRNA.

A number of such designer miRNA precursors will be constructed and cloned into a binary vector under control of a plant promoter using standard cloning techniques. The binary vector containing the designer miRNA precursors will then be introduced into Agrobacterium strains suitable for both transient expression and stable transformation into plant cells. The Agrobacterium-mediated transient expression system as described by Johansen and Carrington (2001) Plant Physiol. 126(3):930-938 or Hamilton et al. (2002) EMBO J 21(17):4671-4679, both of which are herein incorporated by references, will be used in preliminary experiments because it is fast and easy. In these assays, the Agrobacterium culture is pressure-infiltrated into leaf tissues where it is transiently expressed at high levels in a confined region called the "spot" or the "patch". We will use Nicotiana benthamiana expressing the targeted GUS mRNA for the Agro-infiltration experiments. Alternatively, we will transform GUS-expressing Arabidopsis transgenic plants to produce stable transformants that express both the GUS mRNA and the putative GUS miRNA precursor. Stable transformation techniques are well known in the field and are described above.

Step 3. Assay Expression of the Targeted Gene.

Designer miRNA precursors that effectively target the GUS mRNA are capable of altering the expression of the GUS enzyme. GUS enzyme activity will be measured using a standard fluorometric assay. If the miRNA precursor successfully targets the mRNA, a decrease in GUS activity will be observed. Alternatively, since the mechanisms by which miRNAs alter gene expression are not completely understood, it is conceivable that we will observe an increase in GUS activity.

Example 4 miRNA Precursor Designed to Target the GUS mRNA

In a first example of an miRNA precursor designed to target GUS, the backbone for the precursor is amplified by polymerase chain reaction (PCR) from Arabidopsis thaliana genomic DNA using the sequence of the predicted precursor for an endogenous miRNA (miR167). The PCR product is isolated and cloned into the TA cloning vector. The cloned miRNA precursor backbone is further modified by standard cloning techniques to replace the miR167 sequence with the sequence "gcgtaagggt aatgcgaggt ac" which has complete complementarity to a 22 nucleotide region of nucleotides 9978-1000 within the GUS coding region. The entire GUS coding region is 1811 nucleotides. The endogenous 167miRNA sequence is located within the miRNA 167 precursor in a region that forms a double-stranded stem. Therefore, the designer GUS miRNA precursor will be further modified to recreate this region of double-strandedness (so that the GUS miRNA sequence will be located in a double-stranded stein in the precursor).

This construct is cloned into the intermediate vector pRTL2 (Carrington e al. (1990) *EMBO J* 9:1347-53) and then transferred along with the cauliflower mosaic virus 35S promoter and terminator sequences to the binary vector pFA482 (An, G. (1985) *Plant Physiol.* 79:568-570). The binary vector will contain the GUS miRNA precursor under control of the constitutive 35S cauliflower mosaic virus promoter. The vectors are used to transform an *Arabidopsis thaliana* transgenic line that expresses the GUS gene also under control of the 35S promoter. See Anandalakshmi et al. (1998) *Proc Natl Acad Sci USA* 95:13079-13084. The GUS mRNA in this transgenic plant is the target for the GUS miRNA. Transformants carrying both the GUS transgene and the GUS miRNA precursor are examined for GUS activity. GUS activity is decreased or eliminated in plants that express the GUS miRNA precursor. The vectors are also used to transform tobacco via the protocol of An, G. (2002) Plant Molecular Biology Manual, Gelvin and Schulperoot, eds., Kluvwer Academic Publishing, Boston, pp. A-3, 1-19.

In a second example, a GUS miRNA precursor is constructed as described in the above example, but the GUS sequence chosen for the miRNA is complementary to a different region of the GUS mRNA coding region. Plants carrying both the GUS transgene and the second GUS miRNA precursor are observed to have increased GUS activity. Transgenic plants are prepared as described above.

In a third example, GUS miRNA precursor is constructed as described in example 1 above, but the GUS sequence chosen for the miRNA is not completely complementary to the GUS mRNA, containing a three base-pair mismatch in the approximate center of the miRNA. GUS activity in plants carrying both the GUS transgene and the GUS miRNA precursor is reduced or eliminated. Transgenic plants are prepared as described above.

In a fourth example, a GUS miRNA precursor is designed using the backbone from a different predicted endogenous miRNA precursor (miR171). This miRNA precursor backbone is PCR amplified and cloned exactly as described for the miR167 precursor described in example 1 and the miRNA 171 sequences replaced by the 21 nucleotides of sequence complementary to GUS exactly as in example 1. GUS activity in plants carrying both the GUS transgene and the GUS miRNA precursor based on the backbone of miR171 is reduced or eliminated. Transgenic plants are prepared as described above.

Example 5

An miRNA Precursor Designed to Target SULFUR mRNA

An miRNA precursor is designed as described above, but using sequences completely complementary to 21 nucleotides within the coding region of the endogenous SULFUR gene encoding the protein magnesium cheletase. This gene is required for accumulation of chlorophyll in the plant. The SULFUR gene is an example of a reporter gene because, if the expression of the gene is eliminated, the plant will not be green. *Arabidopsis thaliana* plants are transformed with the SULFUR miRNA precursor and transformants carrying the SULFUR miRNA precursor are white. Vectors are constructed and plants are transformed as described in Example 4.

The methods described hereinabove are not limited to use with the GUS gene, other reporter genes, or transgenes. The methods of the invention can be utilized with any other target nucleotide sequence in a plant, including both exogenous and endogenous genes. Similarly, although initial techniques for expressing the designer miRNA precursors in the plant are *Agrobacterium*-mediated transient and stable transformation of *Nicotiana benthamiana* or *Arabidopsis thaliana* plants, the invention is not limited to these plants or these methods of bioengineering plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for transforming a plant cell, the method comprising
   (a) replacing an endogenous miRNA sequence of a nucleotide sequence encoding an isolated plant miRNA precursor with an exogenous miRNA sequence to form a designer miRNA precursor, wherein the exogenous miRNA sequence of the designer miRNA precursor maintains the length of the endogenous miRNA sequence that is replaced;
   (b) modifying additional nucleotides of the nucleotide sequence encoding the isolated plant miRNA precursor, the modified nucleotides being opposite the exogenous miRNA sequence, the modified nucleotides being modified so as to recreate on the designer miRNA precursor a region of double strandedness and mismatches that existed on the nucleotide sequence encoding the isolated plant miRNA precursor prior to replacement of the endogenous miRNA sequence;
   (c) adjusting the G-C content, of the designer miRNA precursor to levels that are average for the plant cell;
   (d) forming an miRNA precursor construct that comprises the designer miRNA precursor; and
   (e) inserting the miRNA precursor construct into the plant cell.

2. The method of claim 1, the miRNA precursor construct comprising a promoter, wherein the promoter is selected from the group consisting of a constitutive promoter, tissue-preferred promoter, and an inducible promoter.

3. The method of claim 2, wherein the promoter is a native promoter of the plant cell.

4. The method of claim 2, wherein the promoter is foreign to the plant cell.

5. The method of claim 1, wherein the exogenous miRNA sequence is from about 15 to about 30 nucleotides in length.

6. The method of claim 1, wherein the exogenous miRNA sequence is completely complementary to a region of a target gene.

7. The method of claim 1, wherein the miRNA comprises a region that is partially complementary to a region of the target gene.

8. The method of claim 1, wherein the miRNA precursor construct is operably linked to a gene to be co-transformed into the plant cell.

* * * * *